United States Patent
Krestel et al.

(10) Patent No.: US 8,921,847 B2
(45) Date of Patent: Dec. 30, 2014

(54) COMPLEXATION OF LOW-MOLECULAR SEMICONDUCTORS FOR THE APPLICATION AS AN EMITTER COMPLEX IN ORGANIC LIGHT-EMITTING ELECTROCHEMICAL CELLS (OLEECS)

(75) Inventors: Ana-Maria Krestel, Erlangen (DE); Günter Schmid, Hemhofen (DE); Dan Taroata, Erlangen (DE); David Hartmann, Erlangen (DE); Wiebke Sarfert, Herzogenaurach (DE)

(73) Assignee: OSRAM GmbH, Munich (DE)

( * ) Notice: Subject to any disclaimer, the term of this patent is extended or adjusted under 35 U.S.C. 154(b) by 0 days.

(21) Appl. No.: 14/008,006

(22) PCT Filed: Mar. 7, 2012

(86) PCT No.: PCT/EP2012/053892
§ 371 (c)(1),
(2), (4) Date: Dec. 23, 2013

(87) PCT Pub. No.: WO2012/130571
PCT Pub. Date: Oct. 4, 2012

(65) Prior Publication Data
US 2014/0103310 A1    Apr. 17, 2014

(30) Foreign Application Priority Data
Mar. 29, 2011    (DE) .................. 10 2011 006 360

(51) Int. Cl.
*H01L 29/08*    (2006.01)
*H01L 51/50*    (2006.01)
*H01L 51/00*    (2006.01)
*H01L 51/56*    (2006.01)

(52) U.S. Cl.
CPC ........ *H01L 51/5032* (2013.01); *H01L 51/0077* (2013.01); *H01L 51/56* (2013.01); *H01L 51/0003* (2013.01)
USPC .................. 257/40; 438/46; 438/99; 428/690

(58) Field of Classification Search
None
See application file for complete search history.

(56) References Cited

U.S. PATENT DOCUMENTS

| | | | |
|---|---|---|---|
| 7,160,012 | B2 | 1/2007 | Hilscher et al. |
| 2005/0179399 | A1 | 8/2005 | Leo et al. |
| 2011/0233593 | A1 | 9/2011 | Kawagoe et al. |
| 2012/0020082 | A1 | 1/2012 | Shinohara |
| 2012/0147624 | A1 | 6/2012 | Li et al. |

(Continued)

FOREIGN PATENT DOCUMENTS

| | | |
|---|---|---|
| DE | 102004002587 B4 | 6/2006 |
| DE | 102009024181 A1 | 12/2010 |

(Continued)

OTHER PUBLICATIONS

International Search Report for PCT/EP2012/053892; dated May 31, 2012; pages.

(Continued)

*Primary Examiner* — Kyoung Lee (57) ABSTRACT

The invention relates to an OLEEC component and to a production process therefor. This component has an active layer including a novel emitter complex. This complex is formed by the coordination of low molecular weight semiconductors around a central cation. The complexation allows wet-chemical processing of low molecular weight semiconductors. This also allows formation of emitter complexes from effective hole or electron transport materials.

16 Claims, 6 Drawing Sheets

(56) References Cited

U.S. PATENT DOCUMENTS

| | | |
|---|---|---|
| 2012/0169213 A1* | 7/2012 | De Cola et al. ............... 313/502 |
| 2012/0230041 A1 | 9/2012 | Mizuta et al. |
| 2013/0035509 A1 | 2/2013 | Schmid et al. |

FOREIGN PATENT DOCUMENTS

| | | |
|---|---|---|
| DE | 102009031683 A1 | 3/2011 |
| DE | 102010005634 A1 | 7/2011 |
| DE | 102011007123 A1 | 10/2012 |
| JP | 2008106015 A | 5/2008 |
| JP | 2012038449 A | 2/2012 |
| WO | 0119765 A1 | 3/2001 |
| WO | 03103067 A2 | 12/2003 |
| WO | 2007004113 A2 | 1/2007 |
| WO | 2007126929 A2 | 11/2007 |
| WO | 2008073542 A1 | 6/2008 |
| WO | 2009054905 A1 | 4/2009 |
| WO | 2011032686 A1 | 3/2011 |

OTHER PUBLICATIONS

Christiane Dietrich-Buchecker et al.; Synthesis of Multi-1, 10-phenanthroline Ligands with 1,3-Phenylene Linkers and Their Lithium Complexes; Chemistry—A European Journal; Jul. 18, 2005; vol. 11, 18.

Denisova, A.S. & Lysinova, M.B.; IR Study of Complexation in the System 1, 10-Phenanthroline-LiCl=4 (NaCl=4)-Acetone; Russian Journal of General Chemistry, vol. 72, No. 6; pp. 823-833; 2002.

* cited by examiner

COMPLEXATION OF LOW-MOLECULAR SEMICONDUCTORS FOR THE APPLICATION AS AN EMITTER COMPLEX IN ORGANIC LIGHT-EMITTING ELECTROCHEMICAL CELLS (OLEECS)

RELATED APPLICATIONS

This application is a national stage entry according to 35 U.S.C. §371 of PCT application No. PCT/EP2012/053892 filed on Mar. 7, 2012, which claims priority from German application No. 10 2011 006 360.9 filed on Mar. 29, 2011.

TECHNICAL FIELD

Various embodiments relate to organic semiconductor components, especially OLEECs, and to the production thereof.

BACKGROUND

In the field of organic semiconductors, organic light-emitting diodes (OLEDs) in particular have become known to date as light-emitting components. A distinction is drawn between OLEDs formed from low molecular weight compounds and OLEDs formed from polymers. While the OLEDs formed from low molecular weight compounds, better known by the term "small molecules", give rise to very efficient components with the aid of multilayer systems, the advantage of polymeric OLEDs lies in the simpler and less expensive manufacturing operations.

The novel component type of light-emitting electrochemical cells shares the inexpensive mode of manufacture of the polymer OLEDs. An OLEEC in the simplest case has only a single active layer comprising various ionic compounds. Only in operation of the component, i.e. only after application of a component voltage, are the negatively charged moieties of the ionic compounds aligned in the direction of the anode, while the positively charged moieties of the ionic compounds are aligned in the direction of the cathode. By means of this ion migration, what is called a p-i-n structure thus forms in the operation of the component, like that which has to be implemented, for example, in the OLED by a multilayer deposition. In this context, p stands for p-conductive, i for intrinsic and n for n-conductive. Predominantly the ions of the so-called matrix material are responsible for the formation of this p-i-n structure. The matrix materials used are preferably ionic liquids. These ions make more of a contribution to the buildup of the internal electrical field in operation than they do to the direct transport of charge.

As well as the matrix material, there is a second ionic component in the active layer. This is usually referred to as the emitter, but, as well as the task of emitting light, equally fulfills the task of the charge transport component. For this purpose, the so-called emitter is present in the active layer in very high concentration, usually well above 50%. The accomplishment of these two tasks, light emission and current transport, places high demands on the emitter material. The latter is very highly stressed in operation, which distinctly shortens its lifetime. Moreover, especially at high luminances, there is triplet-triplet annihilation which greatly lowers the efficiency of the emitter. One reason for the triplet-triplet annihilation can be derived from the knowledge gained in the OLED sector, that it is attributable to the high emitter concentration. However, this cannot be reduced arbitrarily by the present concept.

SUMMARY

Various embodiments specify better emitter materials for OLEECs.

The inventive device is a light-emitting component. This has at least one substrate, a first electrode and a second electrode, and also an active layer. This active layer comprises at least one ionic emitter complex. The ionic emitter complex is selected from a novel emitter class, which has the feature that ligand-centered emission takes place in the complex, meaning that the transition takes place primarily on the ligand. The expression LC (ligand-centered) is commonly used for emitter complexes in which primarily the ligands contribute to the emission thereof; in the simple version, the emission thus arises through π-π* or n-π* transitions. These contrast with intermetallic transitions in phosphorescent emitters. These so-called MLCTs (metal-to-ligand charge transfer) make only an insignificant contribution to the emission in the novel emitter class described.

More particularly, the ionic emitter complex is thus configured such that the proportion of ligand-centered emission is greater than the proportion of emission based on intermetallic transitions. Preferably, the proportion of ligand-centered emission is more than 70%, especially more than 90%.

In an advantageous configuration of the disclosure, the ionic emitter complex comprises at least one central cation and at least one ligand coordinated thereto. This ligand is from the class of the low molecular weight semiconductors, usually called "small molecules". The light-emitting component thus comprises a novel emitter class which is notable particularly for the coordination of small molecules to a central cation.

Examples of low molecular weight semiconductors can be found among the uncharged hole and electron transport materials, as used, for instance, in OLEDs. Hole transporters are based particularly on triarylamines or carbazoles:

Triarylamine    Carbazole

The electron transporters used are especially heterocyclic nitrogen-containing aromatics:

$X = C-H$ or
$X = N$

Suitable coordination sites are the heteroatoms O, S, Se, N or P. These heteroatoms can be utilized for coordination to a positive central ion, especially a metal cation. More particularly, this forms very stable complexes which can also be isolated in pure form. In principle, the positive central ion used may be any metal cation in the periodic table, but particular preference is given to the main group elements of the alkali metal and alkaline earth metal groups, especially lithium, which is very small. Also suitable as the positive central ion are ions such as ammonium or the substituted derivatives thereof.

In one example of a particularly advantageous configuration of the disclosure, the emitter complex has a central lithium cation and phenanthroline ligands coordinated thereto. In alternative forms of these compounds, lithium occurs in pentacoordinate form. Lithium normally coordinates with two bidentate ligands. For example, in a complex in which coordination site 5 is at first occupied by a solvent S, for instance THF, this can be occupied by a hole conductor molecule, for example. It is thus possible by means of a single metal atom, or central cation in general, to combine both electron-conducting and hole-conducting molecular units in one complex:

Particularly preferred solvents S are coordinating solvents such as THF, pyridine or triarylamines, as also find use, for instance, as hole conductors.

Whether tetra- or pentacoordination occurs depends principally on the substituent pattern $R_a$, $R_b$ on the phenanthroline ligand. The substituents $R_a$, $R_b$, $R_x$, $R_y$, $R_z$ may also occur more than once on the molecular skeleton. The substituents $R_a$, $R_b$, $R_x$, $R_y$, $R_z$ may especially each independently be:

methyl radicals,
ethyl radicals, or more generally
unbranched or branched alkyl radicals,
fused (decahydronaphthyl) or cyclic (cyclohexyl) alkyl radicals or
fully or partly substituted alkyl radicals ($C_1$-$C_{20}$).
These alkyl radicals may especially contain:
ether groups (ethoxy, methoxy, etc.),
esters,
amide or carbonate groups etc., or else
halogens, especially F.

Also suitable are substituted or unsubstituted aliphatic rings or ring systems, for instance cyclohexyl.

$R_a$, $R_b$, $R_x$, $R_y$, $R_z$ are not restricted to saturated systems, but also include particularly substituted or unsubstituted aromatics such as:

phenyl,
diphenyl,
naphthyl,
phenanthryl or
benzyl etc.

An illustrative summary of the heterocycles which are possible substituents is also shown below:

Pyrido[3,2-d]pyrimidine pteridine acridine phenezine benzo[g]pteridine 9H-carbazole

Bipyridine & derivatives (0-2 X/ring = N)

For a clearer description, only the base structure of the aromatic system is shown, but it is possible in principle for any of the base structures to be substituted by further R radicals which can be derived analogously from the $R_{1a}$, $R_{1b}$, $R_{2a}$ and $R_{2b}$ radicals defined here. The bond to the ligand may especially be at any position capable of bonding in the base structure.

More particularly, the light-emitting component has an active layer having a matrix material into which the ionic emitter complex has been incorporated. More particularly, this matrix material comprises an ionic liquid. The light-emitting component functions especially as an organic light-emitting electrochemical cell. In this context, the ionic matrix is an essential constituent of the active layer for the formation of a p-i-n structure in the operation of the component. In the electrical field, the anions are aligned in the anode direction and the cations in the cathode direction. However, the actual charge transport is effected via the emitter complex incorporated into the matrix material.

1-methyl-3-(3,3,4,4,5,5,6,6,7,7,8,8,8-tridecafluorooctyl) imidazolium hexafluorophosphate
1-methyl-3-octylimidazolium hexafluorophosphate
1-butyl-2,3-dimethylimidazolium tetrafluoroborate
1-butyl-3-methylimidazolium tetrafluoroborate
1-ethyl-3-methylimidazolium tetrafluoroborate
1-hexyl-3-methylimidazolium tetrafluoroborate
1-methyl-3-octylimidazolium tetrafluoroborate
1-butyl-3-methylimidazolium trifluoromethanesulfonate
1-ethyl-3-methylimidazolium trifluoromethanesulfonate
1,2,3-trimethylimidazolium trifluoromethanesulfonate
1-ethyl-3-methyl-imidazolium bis(pentafluoroethylsulfonyl) imide
1-butyl-3-methylimidazolium bis(trifluoromethylsulfonyl) imide
1-butyl-3-methylimidazolium methanesulfonate
tetrabutylammonium bis-trifluoromethanesulfonimidate
tetrabutylammonium methanesulfonate
tetrabutylammonium nonafluorobutanesulfonate
tetrabutylammonium heptadecafluorooctanesulfonate
tetrahexylammonium tetrafluoroborate
tetrabutylammonium trifluoromethanesulfonate
tetrabutylammonium benzoate
tetrabutylammonium chloride
tetrabutylammonium bromide
1-benzyl-3-methylimidazolium tetrafluoroborate
trihexyltetradecylphosphonium hexafluorophosphate
tetrabutylphosphonium methanesulfonate
tetrabutylphosphonium tetrafluoroborate
tetrabutylphosphonium bromide
1-butyl-3-methylpyridinium bis(trifluoromethylsulfonyl)imide
1-butyl-4-methylpyridinium hexafluorophosphate
1-butyl-4-methylpyridinium tetrafluoroborate sodium tetraphenylborate
tetrabutylammonium tetraphenylborate
sodium tetrakis(1-imidazolyl)borate
cesium tetraphenylborate The matrix materials used may especially also be the guanidinium compounds which follow. These contain, as the central unit, at least one guanidinium unit with positive charge as shown below. The positive charge is naturally delocalized at least within the guanidinium unit:

In order that the OLEEC has a short switching time, an ionic component, especially a salt, is added as a matrix. This component preferably has a low viscosity at room temperature. Materials of this kind are referred to as ionic liquid. Typical representatives are, by way of example but without restriction, as follows:
1-benzyl-3-methylimidazolium hexafluorophosphate
1-butyl-2,3-dimethylimidazolium hexafluorophosphate
1-butyl-3-methylimidazolium hexafluorophosphate
1-ethyl-3-methylimidazolium hexafluorophosphate
1-hexyl-3-methylimidazolium hexafluorophosphate
1-butyl-1-(3,3,4,4,5,5,6,6,7,7,8,8,8-tridecafluorooctyl)imidazolium hexafluorophosphate In these structures, more particularly, all $R_n$ radicals (n=1, 2, 3, 4, 5, 6) are each independently: $R_n$=H, saturated or unsaturated branched alkyl radicals, unbranched alkyl radicals, fused alkyl radicals, cyclic alkyl radicals, fully or partly substituted unbranched, branched, fused and/or cyclic alkyl radicals, alkoxy groups, amines, amides, esters, carbonates, aromatics, fully or partly substituted aromatics, heteroaromatics, fused aromatics, fully or partly substituted fused aromatics, heterocycles, fully or partly substituted heterocycles, fused heterocycles, halogens or pseudohalogens.

All substituents $R_1$, $R_2$, R+ may independently be selected from the abovementioned radicals; these are especially fused alkyl radicals, for example decahydronaphthyl, adamantyl, cyclic, cyclohexyl, or fully or partly substituted alkyl radicals, preferably $C_1$ to $C_{20}$. These chains or groups may bear various end groups, for example charged end groups such as $SO_x^-$, $NR^+$ or others.

The alkyl radicals may in turn bear groups such as ether, ethoxy, methoxy, etc., ester, amide, carbonate, etc., or halogens, preferably fluorine. However, $R_1$, $R_2$ and $R_3$ are not supposed to be restricted to alkyl radicals, but may equally include substituted or unsubstituted aromatic systems, for example phenyl, biphenyl, naphthyl, phenanthryl, benzyl or others.

The substituents $R_1$ to $R_6$ may each independently be aliphatic, aromatic or of complex structure.

By variation of the $R_1$ to $R_6$ radicals, it is possible to produce various kinds of ligand systems. More particularly, the guanidinium matrix materials may include ligands from the selection of all the ligand systems mentioned in this application.

In an advantageous configuration of the disclosure, the low molecular weight semiconductor material is selected from the class of the charge transport materials or emitter materials which, more particularly, typically find use in organic light-emitting diodes. This has the advantage that the emitter complex thus comprises a transport material which contributes to a significant improvement in charge transport in the component. Thus, a novel OLEEC emitter class composed of modified OLED materials is specified.

Typical hole transport materials capable of coordination to a positively charged site are, by way of example but without restriction, as follows:

N,N'-bis(naphthalen-1-yl)-N,N'-bis(phenyl)-9,9-dimethylfluorene
N,N'-bis(3-methylphenyl)-N,N'-bis(phenyl)-9,9-diphenylfluorene
N,N'-bis(naphthalen-1-yl)-N,N'-bis(phenyl)-9,9-diphenylfluorene
N,N'-bis(naphthalen-1-yl)-N,N'-bis(phenyl)-2,2-dimethylbenzidine
N,N'-bis(3-methylphenyl)-N,N'-bis(phenyl)-9,9-spirobifluorene
2,2',7,7'-tetrakis(N,N-diphenylamino)-9,9''-spirobifluorene
N,N'-bis(naphthalen-1-yl)-N,N'-bis(phenyl)benzidine
N,N'-bis(naphthalen-2-yl)-N,N'-bis(phenyl)benzidine
N,N'-bis(3-methylphenyl)-N,N'-bis(phenyl)benzidine
N,N'-bis(3-methylphenyl)-N,N'-bis(phenyl)-9,9-dimethylfluorene
N,N'-bis(naphthalen-1-yl)-N,N'-bis(phenyl)-9,9-spirobifluorene
di-[4-(N,N-ditolylamino)phenyl]cyclohexane
2,2',7,7'-tetra(N,N-ditolyl)aminospirobifluorene
9,9-bis[4-(N,N-bis-biphenyl-4-ylamino)phenyl]-9H-fluorene
2,2',7,7'-tetrakis[N-naphthalenyl(phenyl)amino]-9,9-spirobifluorene
2,7-bis[N,N-bis(9,9-spirobifluoren-2-yl)amino]-9,9-spirobifluorene
2,2'-bis[N,N-bis(biphenyl-4-yl)amino]-9,9-spirobifluorene
N,N'-bis(phenanthren-9-yl)-N,N'-bis(phenyl)benzidine
N,N,N',N'-tetranaphthalen-2-ylbenzidine
2,2'-bis(N,N-diphenylamino)-9,9-spirobifluorene
9,9-bis[4-(N,N-bis(naphthalen-2-yl)amino)phenyl]-9H-fluorene
9,9-bis[4-(N,N'-bis-naphthalen-2-yl-N,N'-bisphenylamino)phenyl]-9H-fluorene
titanium oxide phthalocyanine
copper phthalocyanine
2,3,5,6-tetrafluoro-7,7,8,8-tetracyanoquinodimethane
4,4',4''-tris(N-3-methylphenyl-N-phenylamino)triphenylamine
4,4',4''-tris(N-(2-naphthyl)-N-phenylamino)triphenylamine
4,4',4''-tris(N-(1-naphthyl)-N-phenylamino)triphenylamine
4,4',4''-tris(N,N-diphenylamino)triphenylamine
pyrazino[2,3-f][1,10]phenanthroline-2,3-dicarbonitrile
N,N,N',N'-tetrakis(4-methoxyphenyl)benzidine Typical electron transport materials capable of coordination to a positively charged site are, by way of example but without restriction, as follows:

2,2',2''-(1,3,5-benzinetriyl)-tris(1-phenyl-1-H-benzimidazole)
2-(4-biphenylyl)-5-(4-tert-butylphenyl)-1,3,4-oxadiazole
2,9-dimethyl-4,7-diphenyl-1,10-phenanthroline
8-hydroxyquinolinolatolithium
4-(naphthalen-1-yl)-3,5-diphenyl-4H-1,2,4-triazole
1,3-bis[2-(2,2'-bipyridin-6-yl)-1,3,4-oxadiazo-5-yl]benzene
4,7-diphenyl-1,10-phenanthroline
3-(4-biphenylyl)-4-phenyl-5-tert-butylphenyl-1,2,4-triazole
bis(2-methyl-8-quinolinolato)-4-(phenylphenolato)aluminum
6,6'-bis[5-(biphenyl-4-yl)-1,3,4-oxadiazo-2-yl]-2,2'-bipyridyl
2-phenyl-9,10-di(naphthalen-2-yl)anthracene
2,7-bis[2-(2,2'-bipyridin-6-yl)-1,3,4-oxadiazo-5-yl]-9,9-dimethylfluorene
1,3-bis[2-(4-tert-butylphenyl)-1,3,4-oxadiazo-5-yl]benzene
2-(naphthalen-2-yl)-4,7-diphenyl-1,10-phenanthroline
2,9-bis(naphthalen-2-yl)-4,7-diphenyl-1,10-phenanthroline
tris(2,4,6-trimethyl-3-(pyridin-3-yl)phenyl)borane
1-methyl-2-(4-(naphthalen-2-yl)phenyl)-1H-imidazo[4,5-f][1,10]phenanthroline
4,7-di(9H-carbazol-9-yl)-1,10-phenanthroline
4-(naphthalen-1-yl)-3,5-diphenyl-4H-1,2,4-triazole
4,4'-bis(4,6-diphenyl-1,3,5-triazin-2-yl)biphenyl
1,3-bis[3,5-di(pyridin-3-yl)phenyl]benzene
1,3,5-tri[(3-pyridyl)-phen-3-yl]benzene
3,3',5,5'-tetra[(m-pyridyl)phen-3-yl]biphenyl Examples, without restriction, of coordinatable small emitter molecules are:

3-(2-benzothiazolyl)-7-(diethylamino)coumarin
2,3,6,7-tetrahydro-1,1,7,7-tetramethyl-1H,5H,11H-10-(2-benzothiazolyl)
N,N'-dimethylquinacridone
9,10-bis[N,N-di(p-tolyl)amino]anthracene
9,10-bis[phenyl(m-tolyl)amino]anthracene
bis[2-(2hydroxyphenyl)benzothiazolato]zinc(II)
$N^{10},N^{10},N^{10'},N^{10'}$-tetra-tolyl-9,9'-bianthracene-10,10'-diamine
$N^{10},N^{10},N^{10'},N^{10'}$-tetraphenyl-9,9'-bianthracene-10,10'-diamine
$N^{10},N^{10'}$-diphenyl-$N^{10},N^{10'}$-dinaphthalenyl-9,9'-bianthracene-10,10'-diamine
4,4'-bis(9-ethyl-3-carbazovinylene)-1,1'-biphenyl
1,4-bis[2-(3-N-ethylcarbazoryl)vinyl]benzene
4,4'-bis[4-(di-p-tolylamino)styryl]biphenyl
4-(di-p-tolylamino)-4'-[(di-p-tolylamino)styryl]stilbene
4,4'-bis[4-(diphenylamino)styryl]biphenyl
bis(2,4-difluorophenylpyridinato)tetrakis(1-pyrazolyl)borate iridium (III)
N,N'-bis(naphthalen-2-yl)-N,N'-bis(phenyl)-tris-(9,9-dimethylfluorenylene)
2,7-bis{2-[phenyl(m-tolyl)amino]-9,9-dimethyl-fluorene-7-yl}-9,9-dimethylfluorene
N-(4-((E)-2-(6-((E)-4-(diphenylamino)styryl)naphthalen-2-yl)vinyl)phenyl)-N-phenylbenzenamine
1-4-di-[4-(N,N-di-phenyl)amino]styrylbenzene 1,4-bis(4-(9H-carbazol-9-yl)styryl)benzene
(E)-6-(4-(diphenylamino)styryl)-N,N-diphenylnaphthalen-2-amine
(E)-2-(2-(4-(dimethylamino)styryl)-6-methyl-4H-pyran-4-ylidene)malononitrile
(E)-2-(2-tert-butyl-6-(2-(2,6,6-trimethyl-2,4,5,6-tetrahydro-1H-pyrrolo[3,2,1-ij]quinolin-8-yl)vinyl)-4H-pyran-4-ylidene)malononitrile
2,6-bis(4-(di-p-tolylamino)styryl)naphthalene-1,5-dicarbonitrile
4-(dicyanomethylene)-2-tert-butyl-6-(1,1,7,7-tetramethyljulolidin-4-yl-vinyl)-4H-pyran
4-(dicyanomethylene)-2-methyl-6-(1,1,7,7-tetramethyljulolidyl-9-enyl)-4H-pyran
4-(dicyanomethylene)-2-methyl-6-julolidyl-9-enyl-4H-pyran While the coordination of the low molecular weight semiconductors to the central cation does not adversely affect the conductivity, the complexing operation has a further advantage, namely with regard to the emitter properties of the low molecular weight semiconductors. The fluorescence thereof, which is only very weak particularly in the case of the transport materials, is enhanced by the coordination to such an extent that the complex thus formed can be used as an emitter. The coordination thus only weakly influences the HOMO-LUMO separation, the energy gap between the occupied and unoccupied energy levels in the molecules, such that the conductivity is not impaired, but the transition moment is altered such that the fluorescence intensity rises significantly.

In principle, it is thus possible to make all uncharged fluorescent or else phosphorescent emitters having a coordination site ionic, and hence suitable for OLEECs.

In a further advantageous configuration of the disclosure, the central cation of the emitter complex is a metal cation, an alkali metal cation or alkaline earth metal cation, or an ammonium cation or one of the substituted derivatives thereof.

More particularly, the low molecular weight semiconductor material coordinated in the ionic emitter complex has an energy gap of the same order of magnitude as the uncoordinated, uncharged low molecular weight semiconductor material. This has the advantage that the coordination, i.e. the complexation, of the molecules preserves the conductivity thereof or the propensity thereof to transport charge in an organic layer.

For example, a plurality of uncharged molecules are coordinated to the central cation in the ionic emitter complex. In other words, the extent of the emitter complex is much greater than a single uncharged small molecule.

Thus, the complexation achieves not just a polarization of the molecule but also an "ionization". The transport materials themselves are very nonpolar and are therefore difficult to dissolve. A new species is formed, having entirely different dissolution properties. The complexes have improved solubility and can thus, in contrast to the uncharged small molecules, be processed from solution, for example a sol or an ether solution.

In an advantageous configuration of the disclosure, the light-emitting component has a radiation intensity of at least $5 \times 10^{-5}$ watts per steradian and $m^2$, in a wavelength range between 400 and 500 nm. More particularly, the light-emitting component has a maximum radiation intensity within the wavelength range between 420 and 460 nm, which corresponds to a deep blue color. This is particularly advantageous since none of the emitter complexes known to date for organic electrochemical cells has achieved such an emission color.

The inventive production process for a light-emitting component comprises the following steps: first the synthesis of the ionic emitter complex from the uncharged molecule and a salt of the central cation, then the introduction of this ionic emitter complex into the matrix material, and finally the deposition of the active layer composed of the ionic emitter complex and the matrix material on the first electrode on the substrate. Finally, the second electrode is deposited thereon.

This process has the advantage that the synthesis of the ionic emitter complex from uncharged small molecules makes them suitable for processing from solution. As well as processability from solution, the complexation of the uncharged small molecules holds the further advantage that the excellent charge transport properties thereof can be introduced into the component. Furthermore, the complex molecules have increased fluorescence.

The salts used have, more particularly, simple an ions which are preferably, but without restriction, selected from the following examples:
fluoride,
sulfate,
phosphate,
carbonate,
trifluoromethanesulfonate,
trifluoroacetate,
tosylate,
bis(trifluoromethylsulfon)imide,
tetraphenylborate,
$B_9C_2H_{11}^{2-}$,
hexafluorophosphate,
tetrafluoroborate,
hexafluoroantimonate,
tetrapyrazolatoborate.

Particular preference is given to:
$BF_4^-$,
$PF_6^-$,
$CF_3SO_3^-$,
$ClO_4^-$,
$SbF_6^-$.

Also suitable are complex anions, for example:
$Fe(CN)_6^{3-}$,
$Fe(CN)_6^{4-}$,
$Cr(C_2O_4)^{3-}$,
$Cu(CN)_4^{3-}$,
$Ni(CN)_4^{2-}$.

It has been found experimentally that the halogens chloride, bromide, iodide, in contrast, act as quenchers.

More particularly, the active layer is deposited in a wet-chemical process. Preference is given to the spin-coating process (rotary coating). The layers are generally and preferably deposited from solution, for example including by a printing process, for example inkjet printing, gravure printing or rolling. Suitable solvents here are liquid evaporable organic substances specified by way of example but without restriction hereinafter:
PGMEA=propylene glycol monoethyl ether acetate,
tetrahydrofuran,
dioxane,
chlorobenzene,
diethylene glycol diethyl ether,
diethylene glycol monoethyl ether,
gamma-butyrolactone,
N-methylpyrolidinone,
ethoxyethanol,
xylene,
toluene,
anisole,
phenetole,
acetonitrile.

It is also possible to use further organic and inorganic, and also polar and nonpolar solvents and solvent mixtures.

In addition, it is also possible to introduce polymeric compounds additionally into the solution as matrix material. These can serve, for instance, to improve the semiconductive properties. The addition of a polymer may also serve to improve the film-forming properties, for example in order to achieve a certain minimum layer thickness of the active layer. For example, but without restriction, these may be:

- polyethlene oxides (polyethylene glycols),
- polyethylenediamines,
- polyacrylates such as polymethylmethacrylate (PMMA) or polyacrylic acid or salts thereof (superabsorbents),
- substituted or unsubstituted polystyrenes such as poly-p-hydroxystyrene, polyvinyl alcohols, polyesters or polyurethanes,
- polyvinylcarbazoles,
- polytriarylamines,
- polythiophenes,
- polyvinylidenephenylenes.

The active layer is thus preferably applied from solution, especially to a substrate with a suitable conductive electrode. The first, lower electrode is especially an electrode composed of what is called a TCO, a transparent conductive oxide, for instance indium tin oxide (ITO), aluminum zinc oxide (AZO) or doped tin oxides. The electrode may also have auxiliary layers, for instance for planarization and/or for homogeneous current distribution. Suitable examples include PEDOT:PSS (poly(3,4-ethylenedioxythiophene) poly(styrenesulfonate)) or PANI (polyaniline). After the drying of the active layer, a second, upper electrode is applied as a top electrode. Since the component is a light-emitting component, at least one of the electrodes is transparent. For the second electrode, it is especially also possible to use reflective materials such as magnesium, barium, calcium and aluminum or alloys thereof, noble metals such as silver, gold, copper, but also nickel, chromium, etc.

In an advantageous configuration of the disclosure, the production process comprises the following synthesis steps: first the preparation of a solution of a salt of the central cation, then the preparation of a solution of the uncharged molecule and finally the combination of the two solutions. For the production of the solution of the uncharged small molecule, dichloromethane in particular is used, since these molecules are very sparingly soluble. After the complexation, however, the solubility properties are greatly improved, and there is no longer any need to employ dichloromethane. For dissolution of the finished emitter complex, examples of suitable solvents also include ethers, which are advantageous for the wet-chemical processing and deposition of an organic semiconductor layer.

In a further advantageous configuration of the disclosure, the synthesis includes the combination of the two solutions under protective gas atmosphere. In this case, the solvents are drawn off after the reaction step.

In a further advantageous configuration of the disclosure, the deposition of the active layer is followed by a thermal step for drying. More particularly, the deposition of the second electrode is followed by an encapsulation of the entire layer system which has been applied to the substrate. This encapsulation protects, more particularly, the organic active semiconductor layer from the harmful influence of oxygen or water.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosed embodiments. In the following description, various embodiments described with reference to the following drawings, in which.

DETAILED DESCRIPTION

The following detailed description refers to the accompanying drawing that show, by way of illustration, specific details and embodiments in which the disclosure may be practiced.

There follows a description of four examples of emitter complexes, for which the synthesis is described and test data are disclosed. These are cationic, blue-emitting ammonium and alkali metal complexes having two substituted phenanthroline ligands: 4,7-diphenyl-1,10-phenanthroline and 2,9-dimethyl-4,7-diphenyl-1,10-phenanthroline were used as ligands. Before they are processed, the solvents used are dried, more particularly by a standard procedure.

EXAMPLES 1a AND 1b

Synthesis of the Lithium-Based Metal Complexes

1a) bis(4,7-Diphenyl-1,10-phenanthroline)lithium(I) hexafluorophosphate

1 equivalent of LiPF$_6$ (lithium hexafluorophosphate) (0.073 mmol, 11.14 mg) is dissolved in 2 ml of methanol, and 2.05 equivalents of 4,7-diphenyl-1,10-phenanthroline (0.15 mmol, 50 mg) (purified by sublimation) are dissolved in 5 ml of dichloromethane. A cannula is used to combine the two solutions, and a further 10 ml of freshly distilled oxygen-free tetrahydrofuran are added. The mixture reacts at room temperature under argon atmosphere for 4 hours. After removal of the solvent under reduced pressure, the remaining white-yellowish solid is dissolved in 8 ml of dioxane. The undissolved solid is filtered out. The dioxane solution is dried under reduced pressure. Thereafter, the product is in the form of a milky-white powder (0.056 mmol, 46 mg, 77%).

1b) bis(2,9-Dimethyl-4,7-diphenyl-1,10-phenanthroline)lithium(I) hexafluorophosphate

1 equivalent of LiPF$_6$ (0.067 mmol, 10.29 mg) is dissolved in 2 ml of methanol, and 2.05 equivalents of 2,9-dimethyl-4,7-diphenyl-1,10-phenanthroline (0.138 mmol, 50 mg) (purified by sublimation) are dissolved in 5 ml of dichloromethane. A cannula is used to combine the two solutions, and a further 10 ml of freshly distilled oxygen-free tetrahydrofuran are added. The mixture reacts at room temperature under an argon atmosphere for 4 hours. After the removal of the solvent under reduced pressure, the remaining white-yellowish solid is dissolved in 8 ml of dioxane. The undissolved solid is filtered out and the dioxane solution is dried under reduced pressure. Thereafter, the product is in the form of a milky-white powder (0.044 mmol, 38 mg, 66%).

EXAMPLES 2a AND 2b

Synthesis of the Ammonium-Based Metal Complexes

R = H, CH$_3$

R = H-2a
R = CH$_3$-2b

2a) bis(4,7-Diphenyl-1,10-phenanthroline)ammonium hexafluorophosphate 1 equivalent of ammonium hexafluorophosphate (NH$_4$PF$_6$) (0.075 mmol, 11.96 mg) is dissolved in 2 ml of methanol, and 2.05 equivalents of the 4,7-diphenyl-1,10-phenanthroline ligand (0.15 mmol, 50 mg) (purified by sublimation) are dissolved in 4 ml of dichloromethane. The mixture is then introduced into a 50 ml Schlenk tube and reacts therein at room temperature under an argon atmosphere over the course of several hours. The solvent is then drawn off under reduced pressure and a white powder remains as the product. The product can be used without further purification for the spectroscopic studies.

2b) bis(2,9-Dimethyl-4,7-diphenyl-1,10-phenanthroline)ammonium hexafluorophosphate 1 equivalent of NH$_4$PF$_6$ (0.075 mmol, 11.96 mg) is dissolved in 2 ml of methanol, and 2.05 equivalents of the 4,7-diphenyl-1,10-phenanthroline ligand (0.15 mmol, 50 mg) (purified by sublimation) are dissolved in 4 ml of dichloromethane. The mixture is then introduced into a 50 ml Schlenk tube and reacts therein at room temperature under an argon atmosphere over the course of several hours. The solvent is then drawn off under reduced pressure, and a white powder remains as the product. The product can be used without further purification for the spectroscopic studies.

Figure 1:
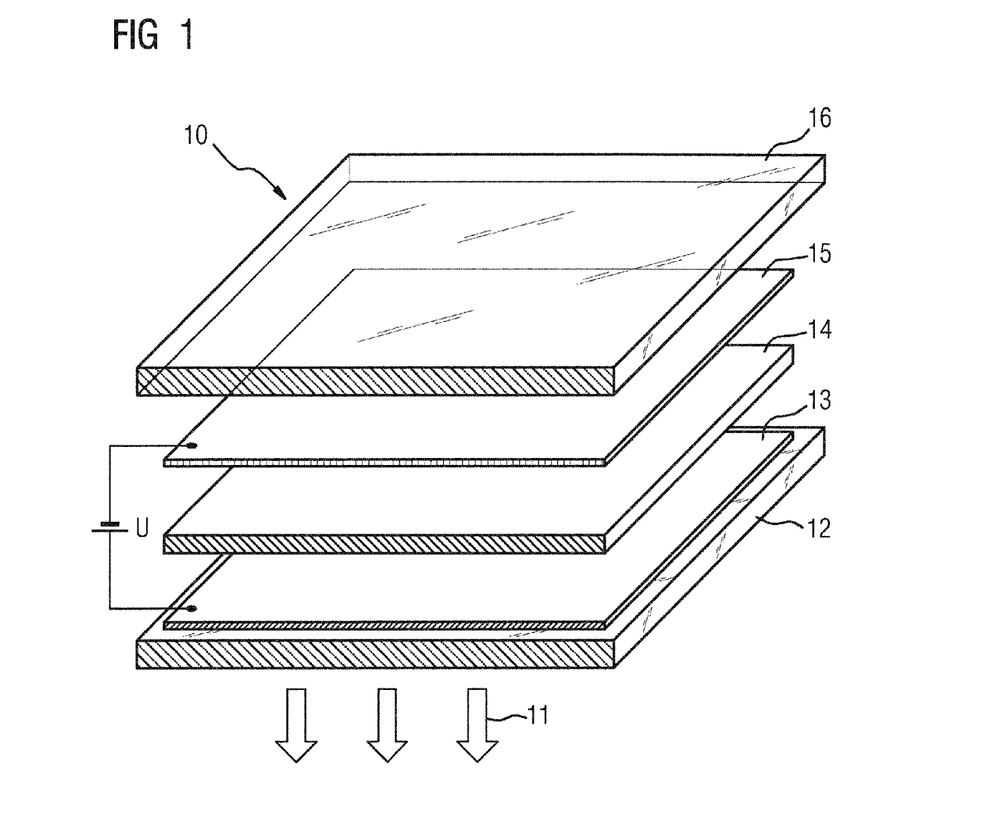
FIG. 1 shows a schematic structure of an OLEEC.

FIG. 1 shows the schematic structure of an organic light-emitting electrochemical cell (OLEEC). FIG. 1 shows the horizontal layers in perspective view, and these are not shown indirect contact with one another for the clarity of the illustration. However, the layers are deposited directly onto one another and are thus in contact with one another over a large area. Starting from the bottom, FIG. 1 shows first the substrate 12, which is especially a glass substrate, but in any case a transparent substrate through which the light 11 generated in the OLEEC can escape. Atop this substrate 12 is an at least semitransparent electrode 13. This is especially an indium tin oxide (ITO) electrode which has been applied directly to the glass substrate, for example by sputtering. The structuring, for example in several pixels, is frequently effected via the structuring of this lower electrode 13. The lower electrode 13 may, however, also consist of several layers. For example, the lower electrode is formed from an ITO layer and a polymer layer. For example, the polymer used is PEDOT:PSS (poly(3,4-ethylenedioxythiophene) poly(styrenesulfonate)). The polymer layer serves, for instance, to level out the ITO electrode and/or to promote hole injection.

In operation, a component voltage U is applied, such that the lower electrode 13 functions as the anode. The lower electrode 13 is followed by the active layer 14 of organic semiconductor material. In this active layer 14, the emitter complex and the matrix material are present. An upper electrode 15 which is applied to this active layer 14 functions especially as the cathode in the component. This upper electrode 15 is, for example, a metal electrode and can be deposited onto the active layer by thermal vaporization.

This upper electrode 15 may then be followed by an encapsulation 16, but the extent thereof is greater than the electrodes 13, 15 and the active layer 14 beneath, and this together with the substrate 12 encloses this layer system such that it is protected from oxygen and water.

An example of an OLEEC described may have the following structure: the active area of the OLEEC component 10 is, for example, 4 mm$^2$, which is defined by the area of the ITO anode 13. The active layer 14 is deposited on ITO glass substrates 12, 13 by means of spin-coating methodology. The aluminum cathode 15 is produced by means of thermal vaporization. A 100 nm PEDOT:PSS layer is incorporated, for example, in order to level out the surface of the ITO anode 13 and to promote hole transport. In that case, the organic emitting layer 14 is thus incorporated, for example, between the PEDOT:PSS layer and the cathode 15. The layer thickness of the aluminum cathode 15 is between 80 and 130 nm. The emission layer 14 is especially prepared as follows: 36 mg of the emitter complex 1b are dissolved together with the matrix material, the ion conductor ($[BMIM]^+[PF_6]^-$), in 0.5 ml of anisole in a molar ratio of 3:1. Before the spin-coating, the solution was filtered with a 0.1 μm PTFE filter. The applied film 14 was dried at 100° C. over the course of 1 hour. Finally, the cathode 15, consisting of 150 to 200 nm of aluminum, was applied by vapor deposition. A subsequent encapsulation 16 protects the organic layer 14 from the interaction with air molecules and water.

Figure 2:
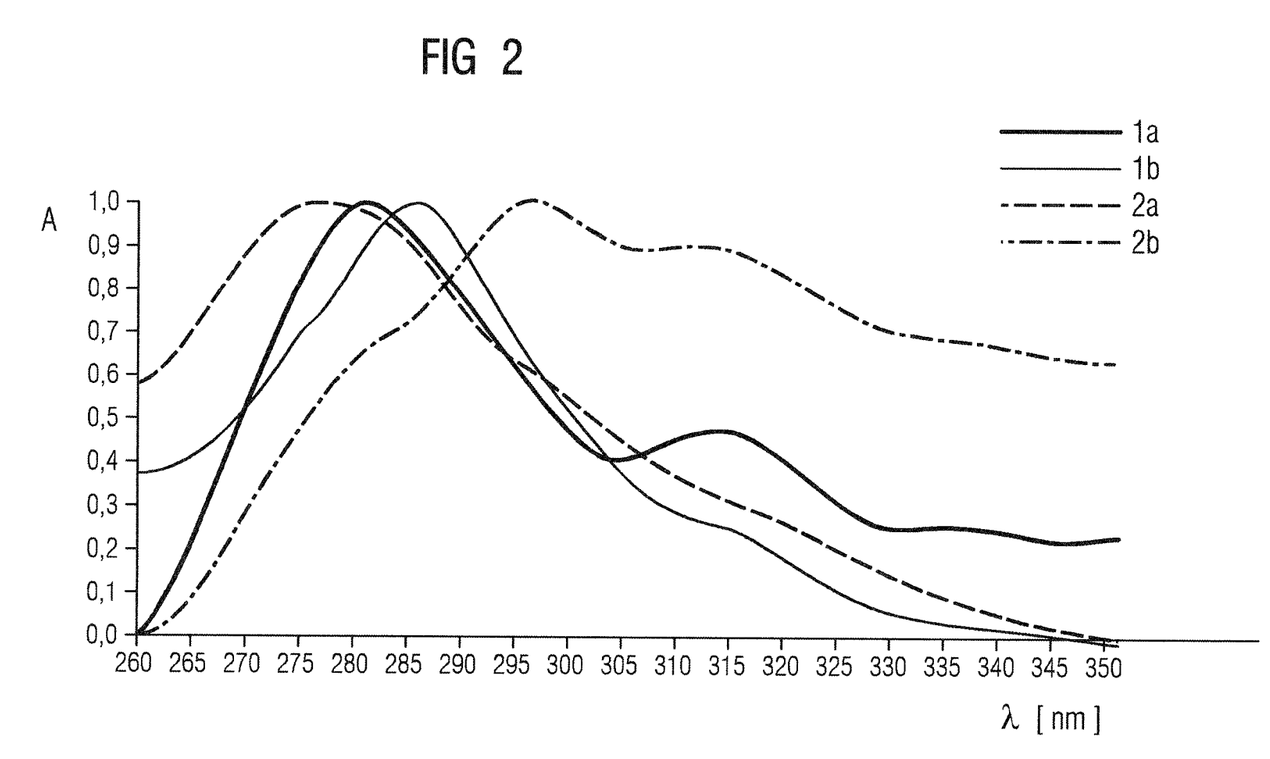
FIG. 2 shows an absorption spectrum of complexes 1a, 1b, 2a and 2b.

FIG. 2 shows the absorption spectrum of the complexes 1a, 1b, 2a and 2b. For the measurement of the absorption A, the complexes are dissolved in DCM (dichloromethane) and were measured at room temperature. In the diagram, the absorption A is plotted in normalized units as a function of the wavelength λ.

Figure 3:
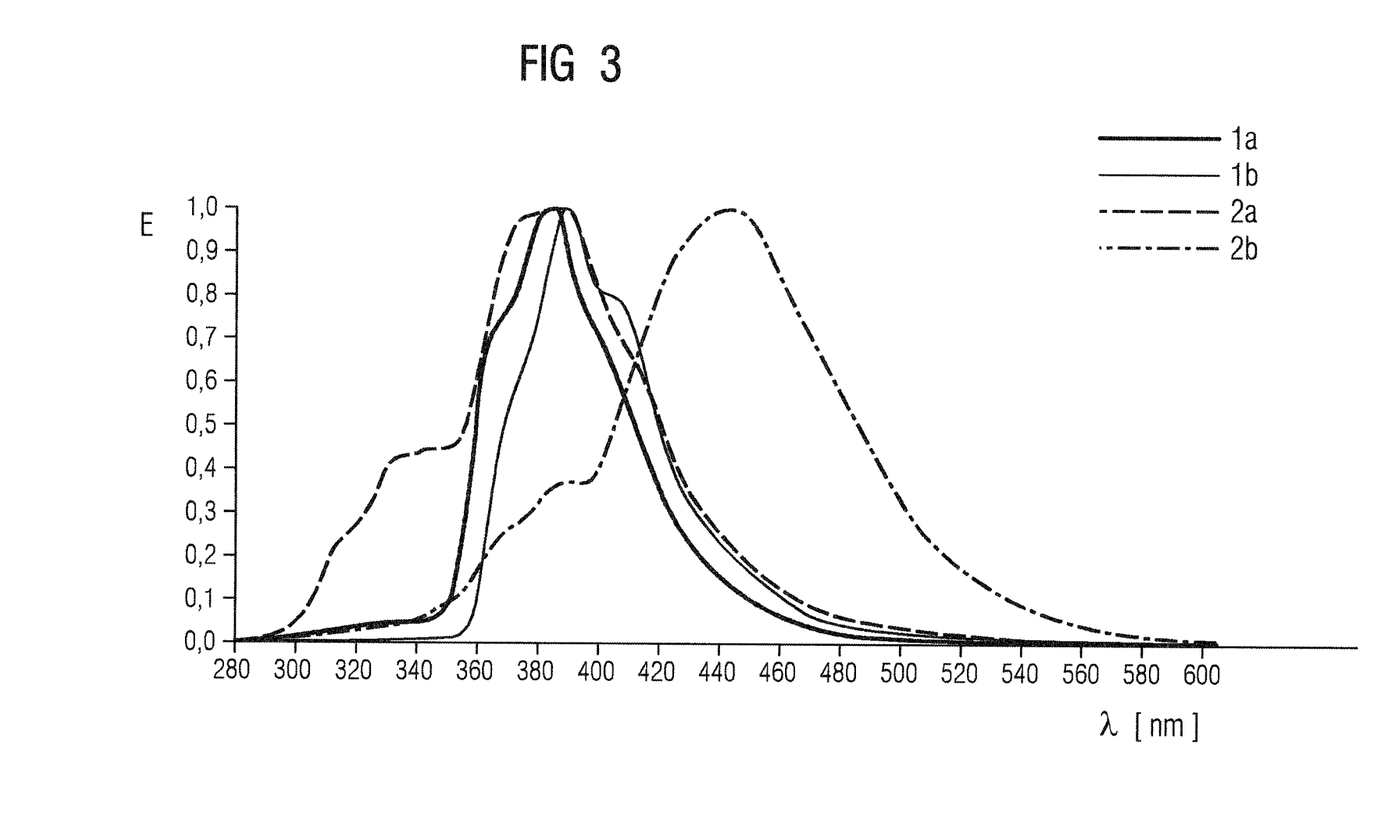
FIG. 3 shows a photoluminescence spectra of complexes 1a, 1b, 2a and 2b.
Figure 4:
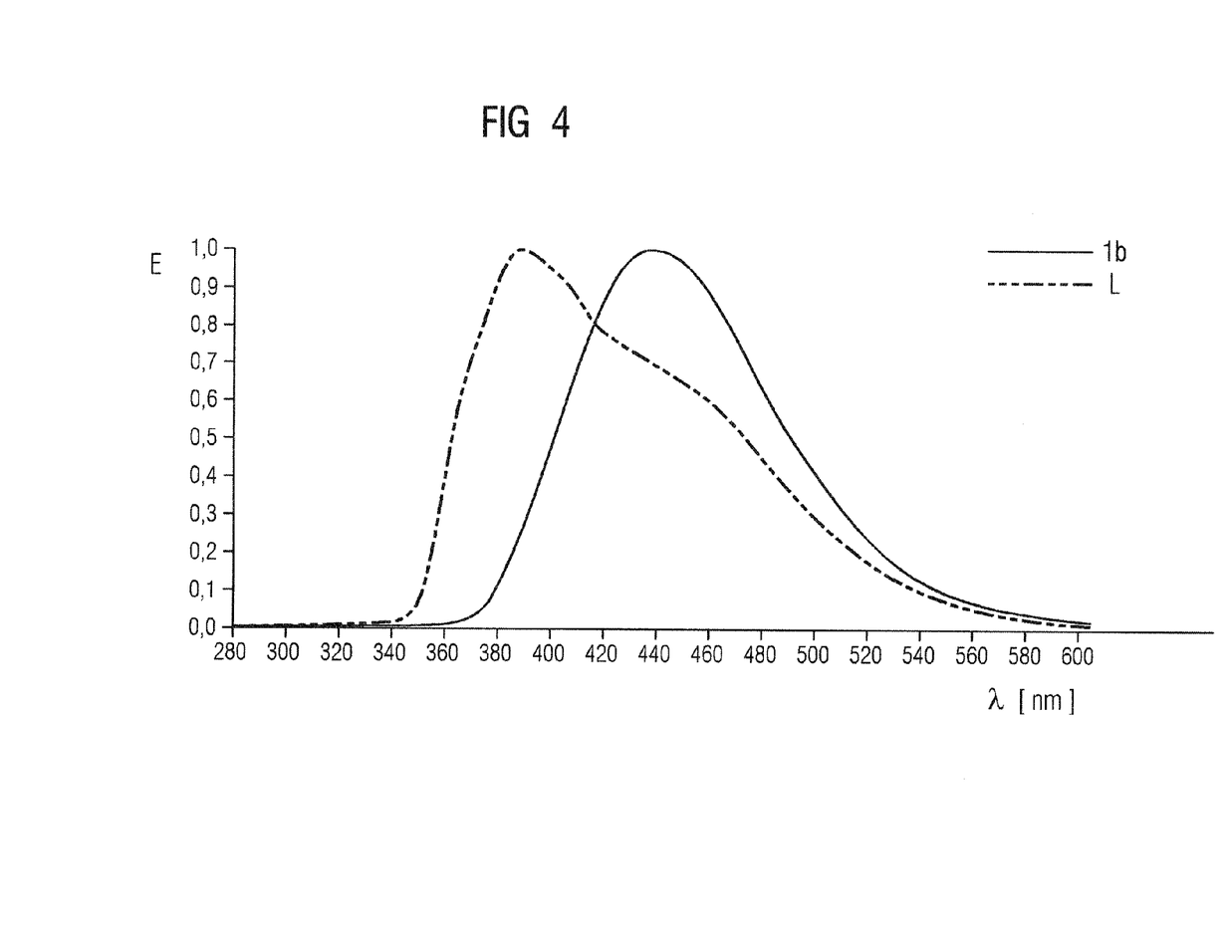
FIG. 4 shows a photoluminescence spectrum of the complex 1b and of a pure ligand.

FIG. 3 shows the corresponding photoluminescence spectra of the same samples, likewise present in a DCM solution and measured at room temperature. All complexes 1a, 1b, 2a and 2b shown have the maximum well below the green wavelength region. FIG. 4 again shows photoluminescence spectra, except that the samples in this case are not in solution; instead, deposited layers on a glass substrate were analyzed. FIG. 4 shows the comparison between the photoluminescence spectrum of complex 1b and the photoluminescence spectrum of ligand L used for complex 1b. This diagram makes it clear that the uncoordinated semiconductor material has maximum emission E in the non-visible region. However, the emitter complex 1b formed with this ligand L emits at a wavelength of 440 nm.

Figure 5:
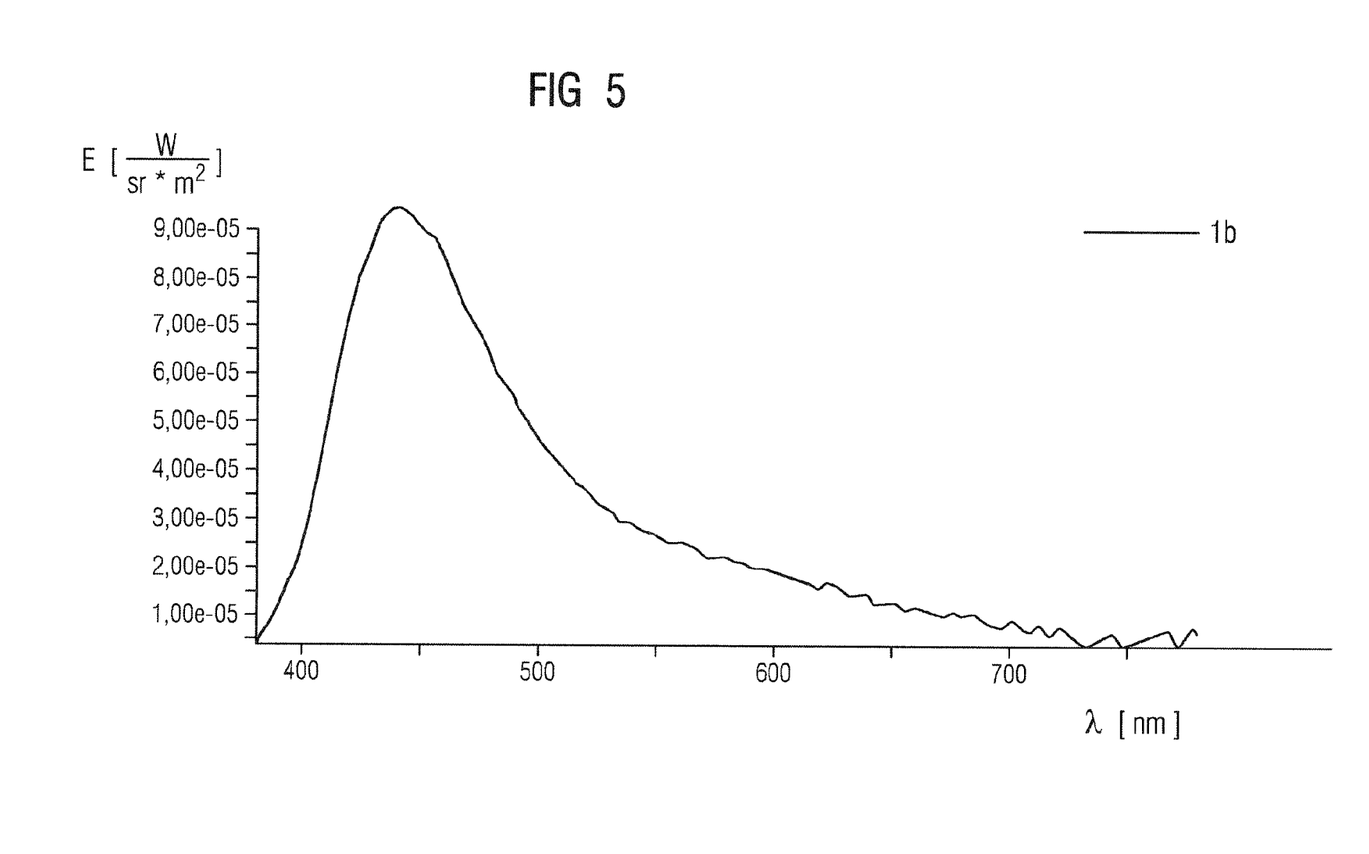
FIG. 5 shows an electroluminescence spectrum of an OLEEC.

FIG. 5 shows the electroluminescence spectrum of an OLEEC with the emitter complex 1b in the active layer. Just like the photoluminescence of the emitter layer, the component in operation also exhibits a maximum emission at 440 nm, which is so high compared to the emission of the other color regions that the component emits in a deep blue color. A spectral camera (PR 650) was used to detect the spectrum in the visible region between 380 and 780 nm. At an applied voltage U of 11 V, the OLEEC comprising the emitter complex 1b emits with a local maximum at 440 nm. The color coordinates of this component in the CIE-1931 diagram (CIE=Commission internationale d'éclairage) are: x=0.19 and y=0.18.

Figure 6:
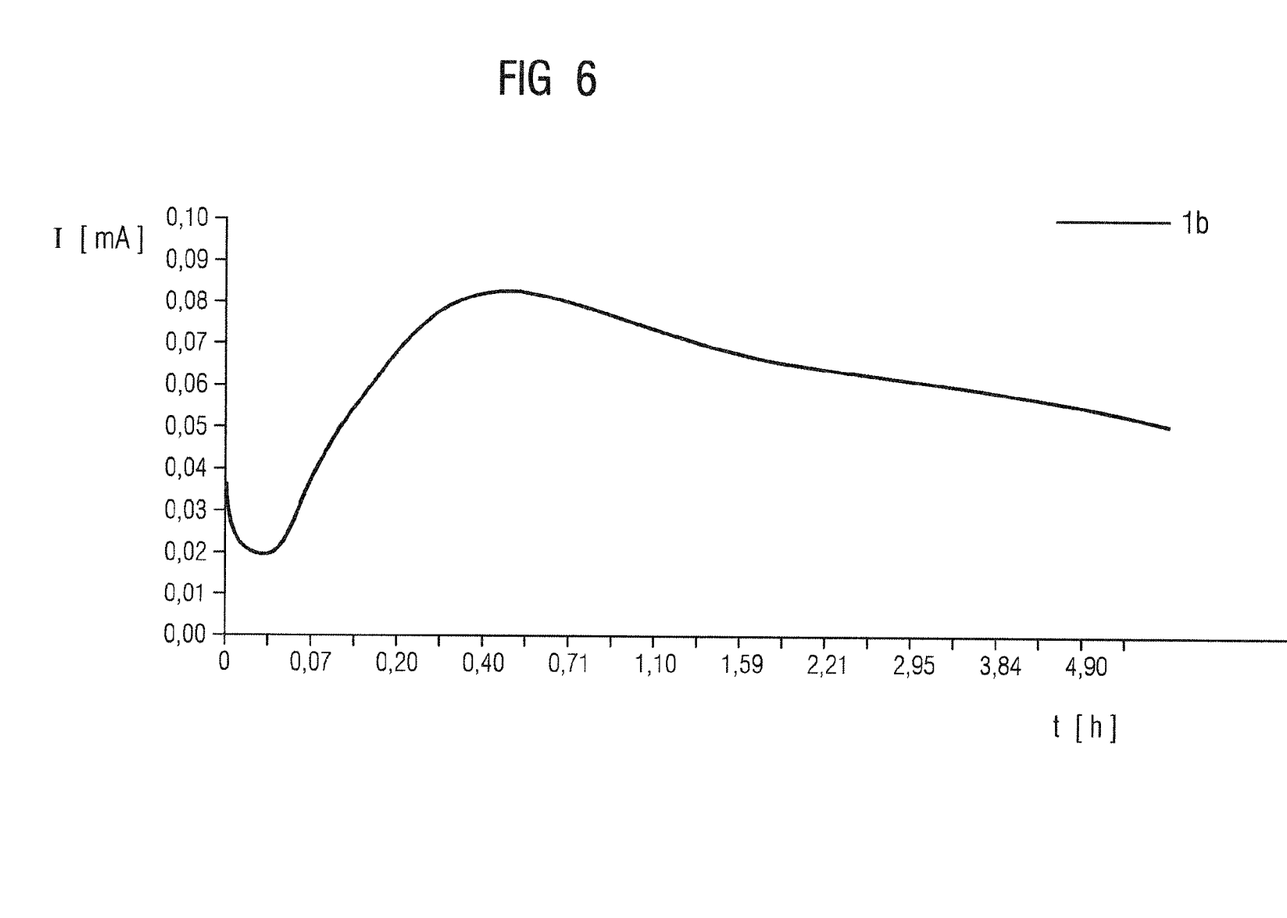
FIG. 6 shows a lifetime measurement, current as a function of time under constant voltage.

Finally, FIG. 6 shows the lifetime characteristics of such a component. For this purpose, at a constant voltage, the current I through the component was measured over the time t.

Here, the voltage U was set to a constant 11 V, and the current was recorded every second. The current-voltage characteristic shows typical behavior of an OLEEC.

While the disclosed embodiments has been particularly shown and described with reference to specific embodiments, it should be understood by those skilled in the art that various changes in form and detail may be made therein without departing from the spirit and scope of the disclosed embodiments as defined by the appended claims. The scope of the disclosed embodiments is thus indicated by the appended claims and all changes which come within the meaning and range of equivalency of the claims are therefore intended to be embraced.

The invention claimed is:

1. A light-emitting component comprising at least one substrate, a first electrode, a second electrode, and an active layer, wherein the active layer comprises at least one ionic emitter complex, the ionic emitter complex being configured for ligand-centered emission.

2. The light-emitting component according to claim 1 working by the principle of an organic electrochemical cell.

3. The light-emitting component according to claim 1, wherein the ionic emitter complex comprises at least one central cation and at least one ligand coordinated thereto, the ligand being a small molecule.

4. The light-emitting component according to claim 1, wherein the active layer comprises a matrix material in which the ionic emitter complex has been incorporated.

5. The light-emitting component according to claim 4, wherein the matrix material comprises an ionic liquid.

6. The light-emitting component according to claim 3, wherein the ligand is a transport material which typically finds use in organic light-emitting diodes.

7. The light-emitting component according to claim 3, wherein the ligand is an emitter material.

8. The light-emitting component according to claim 7, wherein the emitter material is a fluorescent emitter material, which typically finds use in organic light-emitting diodes.

9. The light-emitting component according to claim 3, wherein the central cation is a metal cation, an alkali metal or alkaline earth metal cation or ammonium or substituted derivatives thereof.

10. The light-emitting component according to claim 3, wherein the small molecule coordinated within the ionic emitter complex has an energy gap of essentially the same order of magnitude as the uncoordinated, uncharged small molecule.

11. The light-emitting component according to claim 3, wherein several uncharged small molecules are coordinated to the central cation in the ionic emitter complex.

12. The light-emitting component according to claim 1, wherein the ionic emitter complex is configured such that the proportion of ligand-centered emission is greater than the proportion of emission based on intermetallic transitions.

13. A production process for a light-emitting component, the process comprising:
synthesis of an ionic emitter complex from an uncharged small molecule as a ligand and a salt of a central cation, introduction of the ionic emitter complex into a matrix material, deposition of an active layer on a first electrode on a substrate, and deposition of a second electrode on the active layer.

14. The production process according to claim 13, wherein the active layer is deposited in a wet-chemical process.

15. The production process according to claim 13, wherein the synthesis comprises:

preparing a solution of a salt of the central cation, preparing a solution of the uncharged small molecule, combining the two solutions, the two solutions being combined under protective gas atmosphere, and after the reaction step, removing the solvents.

16. The production process according to claim 13, wherein the deposition of the active layer is followed by a thermal step for drying.

* * * * *

UNITED STATES PATENT AND TRADEMARK OFFICE
CERTIFICATE OF CORRECTION

PATENT NO. : 8,921,847 B2
APPLICATION NO. : 14/008006
DATED : December 30, 2014
INVENTOR(S) : Ana-Maria Krestel et al.

It is certified that error appears in the above-identified patent and that said Letters Patent is hereby corrected as shown below:

In the Specification

Column 4, line 49, delete "1,3-benzosazole" and write "1,3-benzoxazole" in place thereof.

Column 5, line 12, delete "phenezine" and write "phenazine" in place thereof.

Column 7, line 41, delete "9,9'"" and write " 9,9'" in place thereof.

Column 8, line 29, delete "10-phenantro line" and write "10- phenantroline" in place thereof.

Signed and Sealed this
Second Day of June, 2015

Michelle K. Lee
*Director of the United States Patent and Trademark Office*